US00PP30892P3

(12) United States Plant Patent
Probasco et al.

(10) Patent No.: US PP30,892 P3
(45) Date of Patent: Sep. 24, 2019

(54) HOP PLANT NAMED 'HBC 644'

(50) Latin Name: *Humulus lupulus*
Varietal Denomination: HBC 644

(71) Applicant: HOP BREEDING COMPANY, L.L.C., Yakima, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/732,377

(22) Filed: Oct. 31, 2017

(65) Prior Publication Data

US 2018/0160599 P1 Jun. 7, 2018

Related U.S. Application Data

(60) Provisional application No. 62/496,933, filed on Nov. 1, 2016.

(51) Int. Cl.
*A01H 5/08* (2018.01)
*A01H 5/02* (2018.01)

(52) U.S. Cl.
USPC ..... Plt./236
CPC ..... *A01H 5/02* (2013.01)

(58) Field of Classification Search
USPC ..... Plt./236
CPC ... A01H 5/08; A01H 5/02; A01H 5/12; A01H 5/00; A01H 6/28; A01H 6/00
See application file for complete search history.

*Primary Examiner* — June Hwu
(74) *Attorney, Agent, or Firm* — Svendsen Legal, LLC

(57) ABSTRACT

A new hop plant named 'HBC 644' is disclosed. 'HBC 644' is used for its exceptional and unique aromatic qualities.

6 Drawing Sheets

Genus and species: *Humulus lupulus*.
Variety denomination: 'HBC 644'.

STATEMENT REGARDING FEDERALLY SPONSORED RESEARCH OR DEVELOPMENT

None

BACKGROUND OF THE INVENTION

'HBC 644' is a product of a controlled breeding program carried out by the inventors in the Yakima Valley of Washington State. 'HBC 644' was one of several seedlings resulting from a open pollination cross made in 2008 with female parent 'CoLT' (unpatented), and an unknown male parent. The 'CoLT' cultivar was created through a chromosomal doubling of the 'COLUMBUS' (U.S. Plant Pat. No. 10,956) cultivar, which has a diploid ploidy. The most distinguishing characteristic between the instant cultivar, its maternal parent ('CoLT'), and a comparison cultivar ('COLUMBUS') is the ploidy of each cultivar. The instant cultivar has a triploid ploidy, while its maternal parent 'CoLT' has a tetraploid ploidy, and the 'COLUMBUS' cultivar has a diploid ploidy.

Seedling plants from this cross were planted in 2009 and screened for disease resistance and sex in a greenhouse and field nursery near Granger, Wash. A single plant of 'HBC 644' was selected in 2012 and was asexually reproduced via softwood cuttings in a greenhouse near Toppenish, Wash. In 2013 'HBC 644' was expanded by asexual reproduction via softwood cuttings to 14 plants in an evaluation block near Toppenish, Wash. In 2015 'HBC 644' was further expanded by asexual reproduction via softwood cuttings to a 1 acre test block near Toppenish, Wash. The 'HBC 644' plants have now been observed and evaluated for several years.

Throughout several generations of asexual propagation, 'HBC 644' has been observed to retain its distinctive characteristics and remain true to type.

COMPARISON OF 'HBC 644' TO PARENT PLANT AND COMARISON CULTIVAR

Table 1. below, sets forth some of the distinguishing characteristics of 'HBC 644' as compared to its female parent 'CoLT', and to the 'COLUMBUS' cultivar as a closely comparable cultivar.

TABLE 1

| | INSTANT CV. 'HBC 644' | FEMALE PARENT 'CoLT' | COMPARISON CV. 'COLUMBUS' |
|---|---|---|---|
| Ploidy | Triploid | Tetraploid | Diploid |
| Alpha (% of cone weight) | 11.9-14.9 | not available | 14.5-17.5 |
| Beta (% of cone weight) | 3.5-3.9 | not available | 4.5-6.0 |
| Co-humulone (% of alpha acids) | 28.5-30.5 | not available | 28-30 |
| Total Oil (mL/100 g) | 2.3-2.8 | not available | 2.5-4.5 |
| Aroma Profile | pine, citrus, spicy | not available | earthy, citrus, spicy |

BRIEF DESCRIPTION OF THE PHOTOGRAPHS

Figure 1:
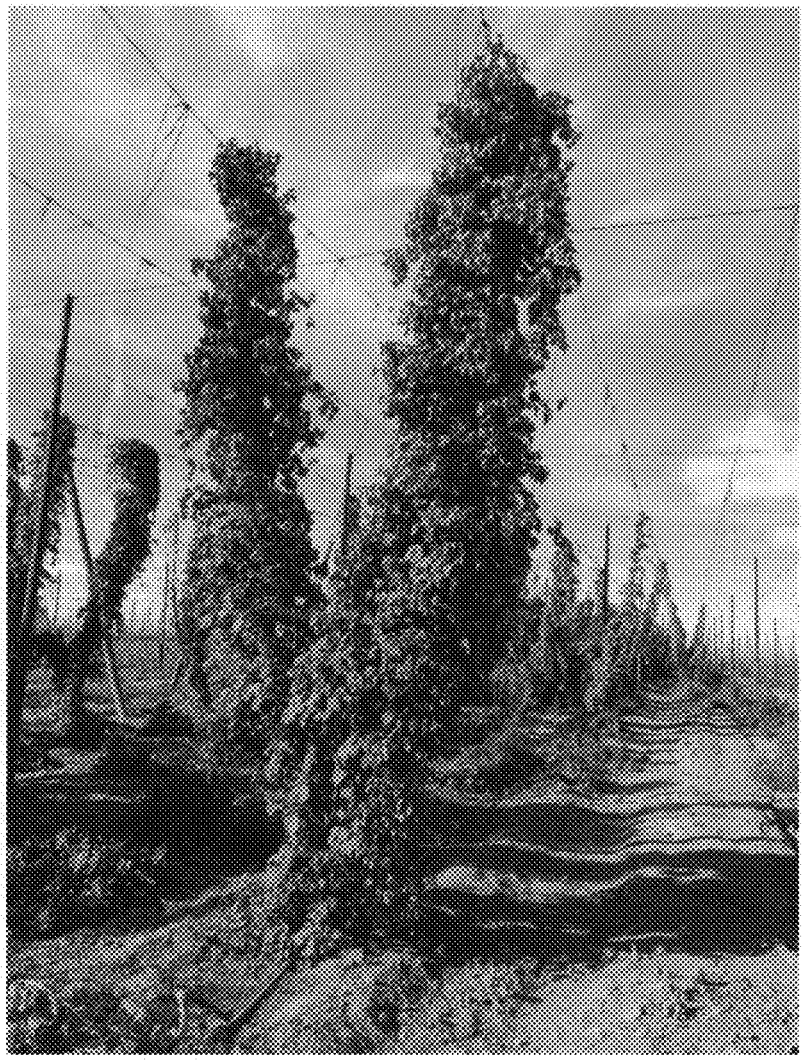
FIG. 1 illustrates a mature 'HBC 644' hop plant grown on a trellis.
Figure 2:
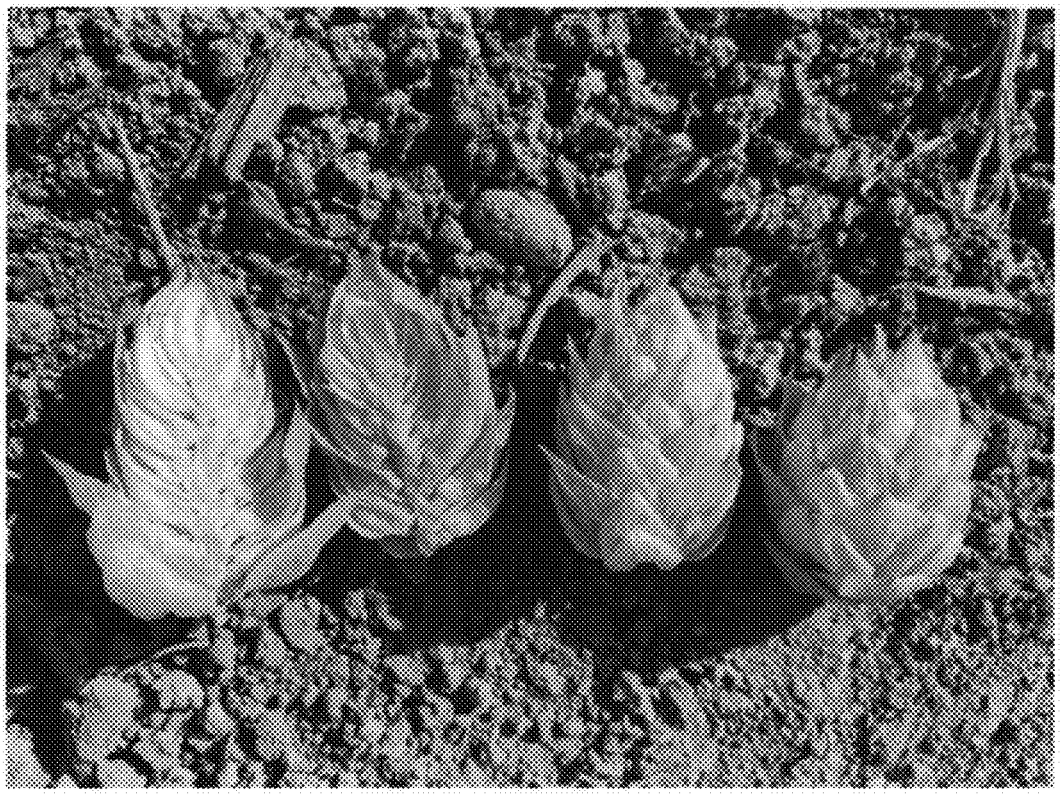
FIG. 2 illustrates whole cones and cross sections of cones of the 'HBC 644' hop plant.
Figure 3:
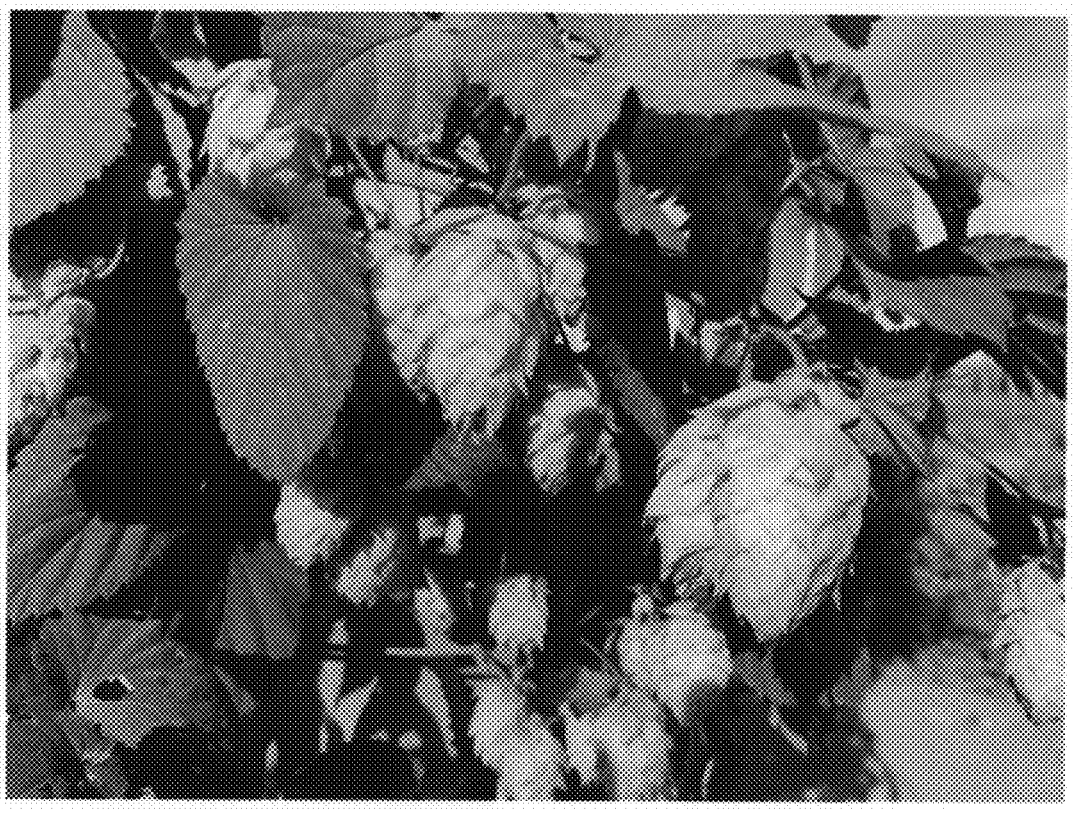
FIG. 3 illustrates cones on a mature 'HBC 644' hop plant.
Figure 4:
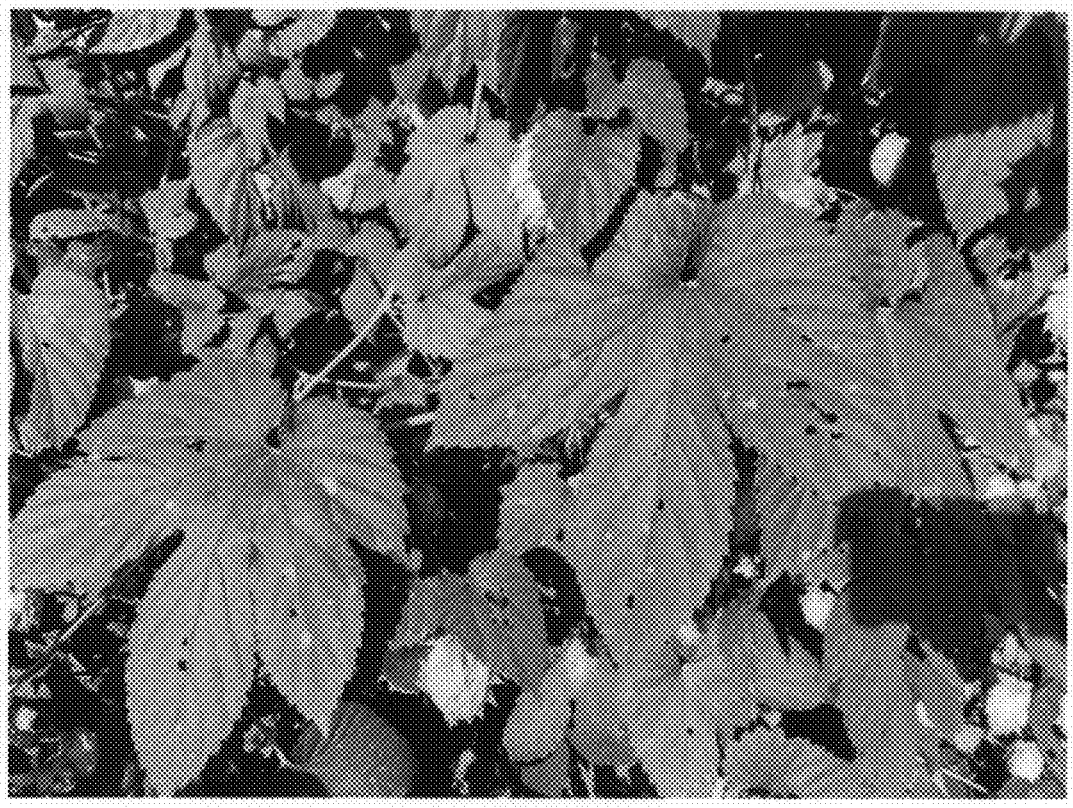
FIG. 4 illustrates leaves on a mature 'HBC 644' hop plant.
Figure 5:
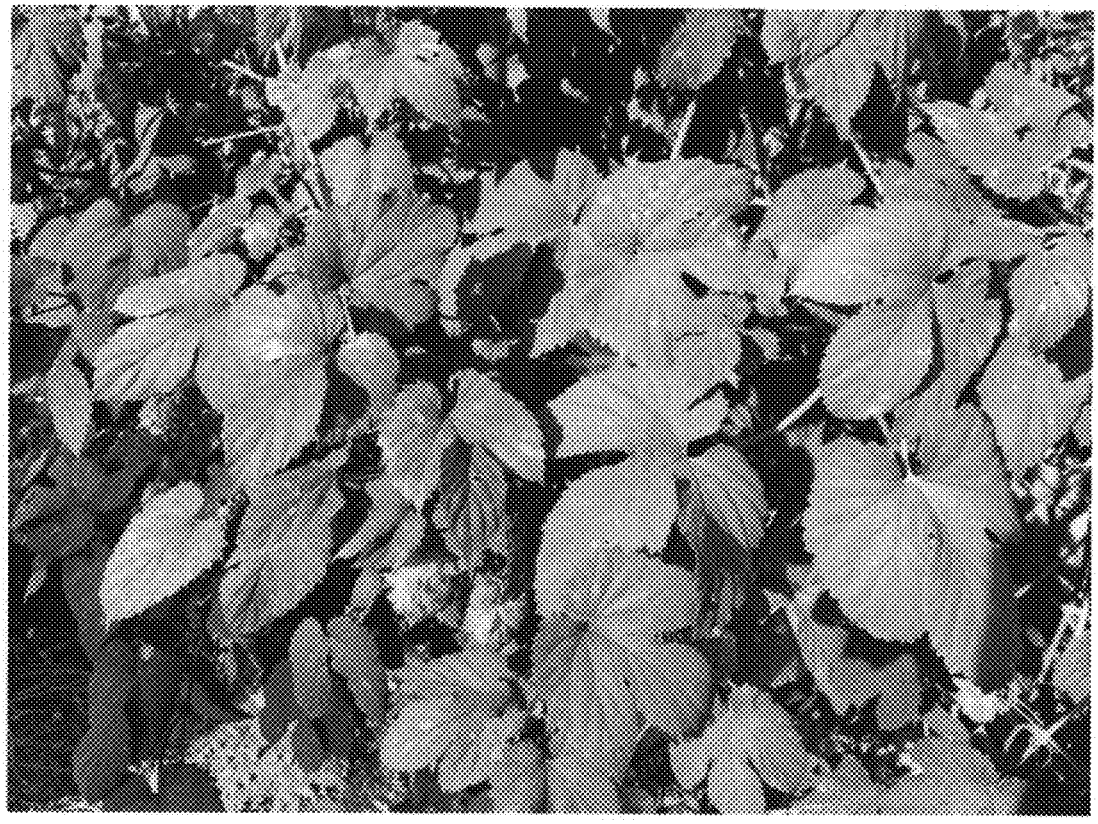
FIG. 5 illustrates leaves of a mature 'HBC 644' hop plant.
Figure 6:
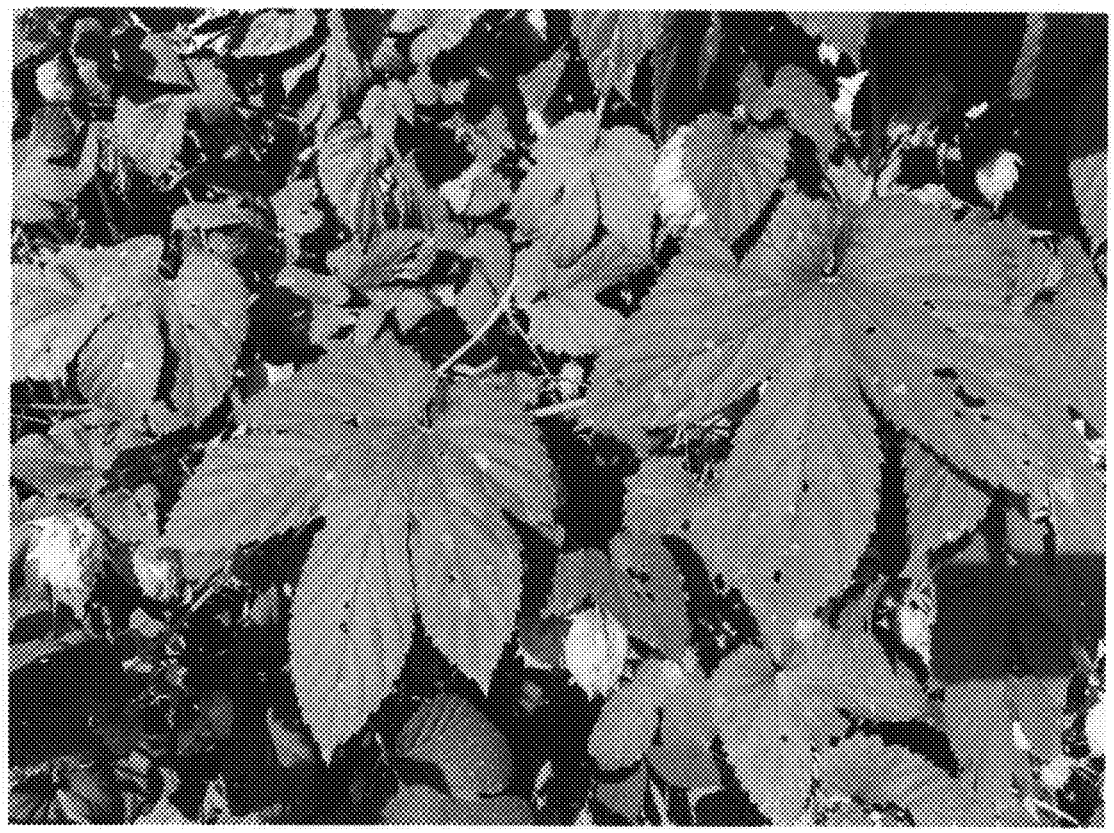
FIG. 6 illustrates leaves of a mature 'HBC 644' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2016 growing season at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on the 2001 edition of The Royal Horticultural Society Colour Chart.

Ploidy: Triploid.

Sex: Female.

Use: Brewing beer and ale.

Harvest date: September 20 to 30 (during 2015 to 2016 growing seasons at Toppenish, Wash.).

Yield: Average yield is 2450 kg/hectare to 2900 kg/hectare.

Disease reaction:

*Powdery mildew.*—Moderate resistance.

*Downy mildew.*—Unknown.

*Verticillium wilt.*—Unknown.

TABLE 2

| Oil Analytical Characteristics (Averages): | |
|---|---|
| % Alpha Acid (% cone weight) | 11.9-14.9 |
| % Beta Acid (% cone weight) | 3.5-3.9 |
| % Cohumulone (% alpha acids) | 28.5-30.5 |
| Total Oil (ml/100 g of cones): | 2.3-2.8 |
| Hop Storage Index | <35%-45% |
| Aroma Profile | Sulfur, pine, citrus, spicy |
| A-Pinene: | 0.09% Total Oil |
| B-Pinene: | 0.65% Total Oil |
| Myrcene: | 42.69% Total Oil |
| 2-methyl-butyl isobutyrate: | 0.51% Total Oil |
| Limonene: | 0.19% Total Oil |
| Linalool: | 0.52% Total Oil |
| Caryophyllene: | 10.21% Total Oil |
| Farnesene: | 0.05% Total Oil |
| Humulene: | 17.18% Total Oil |
| Citral: | 0.79% Total Oil |
| Geranyl Acetate: | 0.96% Total Oil |
| Citronellol: | 2.88% Total Oil |
| Nerol: | 0.34% Total Oil |
| Geraniol: | 0.19% Total Oil |
| B-lonene: | 0.01% Total Oil |

Plant growth type: Climbing Bine, Normal (not dwarf), Cylindrical.

Anthocyanin coloration of bine: Very Weak to Weak.

Hardiness: Observed Plant Hardiness Zone 7a.

Freeze tolerance: Typically intolerant of freezing temperatures during the growing season.

Bine:

*Color.*—Yellow-Green 144B.

*Stripe present.*—No.

*Stripe color.*—N/A.

*Stipule direction.*—Up.

*Average number of stipule per bine.*—Two per node.

*Bine diameter.*—8.5 mm at base; 11 mm at nine feet; 6.0 mm at terminal end of eighteen feet.

*Typical and observed bine length.*—Typical bine growth of 19 feet to 23 feet, when grown on a standard eighteen foot trellis.

Lateral:

*Lateral length.*—On average, 87 cm to 150 cm.

*Lateral density.*—2 laterals per node.

Leaf:

*Arrangement.*—Opposite.

*Shape.*—Palmately Lobed.

*Average length of mature leaf.*—13.0 cm.

*Average width of mature leaf.*—18.4 cm.

*Color of mature leaf upper surface.*—Yellow-Green 147A.

*Color of mature leaf lower surface.*—Yellow-Green 147B.

*Color of immature leaf upper surface.*—Green 137A.

*Color of immature leaf lower surface.*—Yellow-Green 147B.

*Number of lobes.*—3 or 5.

*Margin.*—Serrate.

*Serrations per inch.*—3 to 6.

*Average petiole length (mature).*—63 mm.

*Petiole color at base.*—Yellow-Green 187B.

*Venation.*—Palmate.

*Vein color.*—Yellow-Green 146D.

Cone:

*Avg. length.*—30 mm.

*Avg. diameter.*—19 mm.

*Bract tip color.*—Yellow-Green 144A.

*Bract base color.*—Yellow-Green 145B.

*Bracteole color.*—Yellow-Green 145C.

*Cone shape.*—Ovate.

*Cone tip shape.*—Acute.

*Average cone weight.*—700 mg to 1200 mg.

*Bract shape.*—Orbicular.

*Bract tip shape.*—Acuminate-Mucronate.

*Bract tip position.*—(not observed).

*Bract average length.*—15 mm to 20 mm.

*Bract average width.*—14 mm to 18 mm.

*Bracteole average length.*—14 mm to 18 mm.

*Bracteole average width.*—9 mm to 12 mm.

*Bracteole shape.*—Oval.

*Observed appearance of female inflorescences.*—Middle to Late July.

*Pickability.*—Good.

*Lupulin glands color.*—Yellow 2A.

The invention claimed is:

1. A new and distinct Hop plant as illustrated and described herein.

* * * * *